US 6,628,381 B1

(12) United States Patent
Komem et al.

(10) Patent No.: US 6,628,381 B1
(45) Date of Patent: *Sep. 30, 2003

(54) OPTICAL INSPECTION METHOD AND APPARATUS UTILIZING A COLLECTION ANGLE DESIGN

(75) Inventors: Amir Komem, Ramat Gan (IL); Erel Milshtein, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 09/595,902

(22) Filed: Jun. 20, 2000

(51) Int. Cl.[7] .............................................. G01N 21/88
(52) U.S. Cl. .................................................. 356/237.4
(58) Field of Search ............................ 356/237.4, 237.5

(56) References Cited

U.S. PATENT DOCUMENTS

| | | | |
|---|---|---|---|
| 4,898,471 A | * 2/1990 | Stonestrom et al. | ........ 356/394 |
| 5,076,692 A | * 12/1991 | Neukermans et al. | ....... 356/394 |
| 5,276,498 A | 1/1994 | Galbraith et al. | |
| 5,604,585 A | 2/1997 | Johnson et al. | |
| 6,256,093 B1 | * 7/2001 | Ravid et al. | ............. 356/237.4 |

* cited by examiner

*Primary Examiner*—Richard A. Rosenberger
(74) *Attorney, Agent, or Firm*—Sughrue Mion LLP.

(57) ABSTRACT

Method and apparatus for optical inspection of a patterned article are presented. A region on the article is illuminated with incident light to produce light returned from the illuminated region. An image of the illuminated region is acquired and analyzed for determining the intensity distribution of light components scattered from the pattern of the illuminated region within a certain collection angular field located outside a solid angle of propagation of specularly reflected light. Based on the determined distribution, light components scattered from the illuminated region and propagating with at least one predetermined solid angle segment of the certain collection angle are collected and directed to a dark-field detection unit.

21 Claims, 8 Drawing Sheets

OPTICAL INSPECTION METHOD AND APPARATUS UTILIZING A COLLECTION ANGLE DESIGN

FIELD OF THE INVENTION

The present invention is in the field of optical inspection techniques and relates to a method and an apparatus for inspecting patterned articles, such as integrated circuits, printed circuit boards, photolithographic masks, liquid crystal displays, etc., utilizing a collection angle design.

BACKGROUND OF THE INVENTION

A typical structure of the patterned article, such as a semiconductor wafer, includes a basic cell element repeated numerous times in both lateral dimensions, creating an almost perfectly periodical two-dimensional pattern, Semiconductor wafers are inspected prior to and after a pattering procedure, since the timely detection of anomalies on the wafer's surface is a very important factor, subsequently leading to an increase in production yields.

The prior-to-patterning inspection of wafers relies on the fact that light is scattered mainly from anomalies present on the generally flat and smooth surface of the non-patterned wafer. Thus, any detection of scattered light may be indicative of a defect. When applying an optical inspection to a patterned wafer aimed at detecting defects (e.g., the existence of foreign particles), scattered light can be caused by the pattern. Therefore, the detection of scattered light is not necessarily indicative of a defect. Conventional techniques for detecting defects are the so-called "die-to-database" and "die-to-die" techniques, according to which light scattered from an individual die is compared to, respectively, the previously prepared database indicative of light scattered from the "non-defective" die and a "neighbor" of this individual die. Differences between the signals are indicative of light scattered from anomalies present on the surface of the article. Generally speaking, detected difference in light components scattered from the individual die is indicative of the absence or addition of some features in this die, as compared to the "non-defective" die or "neighbor" die, and is therefore considered to be a defect.

An optical inspection apparatus is typically composed of such main constructional parts as an illumination system and a light collection/detection system utilizing either a bright field or dark field mode. The bright field detection mode is based on the variability in the specular reflectance from the wafer under inspection, created by defects squandered on the wafer. The dark field detection mode uses the scattering from defects that does not orient in specular reflectance.

It is a common goal of the collection scheme to increase the signal-to-noise ratio of the detected signal as much as possible. Various forms of dark field detection schemes are found to be very effective for the purpose of defect detection. According to one known technique of this kind, disclosed in U.S. Pat. Nos. 4,898,471 and 5,604,585, to facilitate meaningful signal comparison, the light collection system collects light at one constant collection angle at the azimuth and elevation other than those where the specular reflection occurs. However, light scattered from the patterned article (e.g., wafer) always contains light components scattered from the pattern towards this collection angle, and, therefore, detection of these light components is indicated by increased "noise" in the detected signal.

SUMMARY OF THE INVENTION

The present invention is aimed at improving automatic optical inspection of patterned articles by providing a novel method and apparatus enabling the signal-to-noise ratio of detected signals to be significantly increased.

The present invention takes advantage of a technique utilizing a variable angle design of the light collection system. This technique is disclosed in a co-pending application assigned to the assignee of the present application. According to this technique, an article (e.g., wafer) under inspection is scanned region-by-region, light scattered from each of the scan regions is collected with a certain maximum collection angle constant for each scan region, and directed towards a detection means trough a filter. The latter is selected such as to pick up from the entire collected light only that part thereof propagating with a solid angle segment of the entire collection angle, where the intensity of light scattered from the pattern is minimal, as compared to other solid angle segments of the maximum collection angle. This enables to increase the signal-noise ratio of the detected signal. The detection means comprises at least one detection unit operating in a dark field imaging mode, i.e. collecting light components scattered from the article at the azimuth and elevation different from those where the most specular reflection occurs.

The main idea of the present invention consists of selecting the variable angle solution. This is implemented by acquiring a bright field or high resolution dark field image and analyzing the acquired image to determine a solid angle segment of the propagation of light returned from the pattern within the collection angular field. This enables customized light collection (CLC) to be applied to dark field scattering signals, so as to prevent that part of the scattered signals, which is associated with the pattern on the article and constitutes "noise", from reaching the detector, thereby allowing the detection of only that part of the scattering signals which is associated with any feature in the illuminated region other than those of the pattern. In other words, a suitable mask is placed in the optical path of light scattered from the article and propagating towards a dark field detector, such that the mask cuts off the solid angle segment of propagation of light scattered from the pattern. This results in a significant increase in the signal-to-noise of the detected signals.

Thus, according to one aspect of the present invention, there is provided a method for optical inspection of a patterned article, the method comprising the steps of:

(i) illuminating a region on the article with incident light to produce light returned from the illuminated region;

(ii) acquiring an image of the illuminating region, and generating data representative thereof;

(iii) analyzing the generated data and determining intensity distribution of light components scattered from the pattern of the illuminated region within a certain collection angular field outside a solid angle of propagation of specularly reflected light;

(iv) based on the determined distribution, filtering light collected with said certain collection angular field, so as to collect light components scattered from the illuminated region and propagating with at least one predetermined solid angle segment of said certain collection angular field, and to direct the collected light components to a detection unit.

The term "collection angular field" used herein signifies a maximum solid angle of collection of light scattered from the article defined by an optical arrangement of the detection unit.

In step (ii) above, light detected for acquiring the image of the illuminated region may be that specularly reflected from the illuminated region (i.e., bright field detection mode) or the scattered light propagating with a solid angle outside the solid angle of propagation of specularly reflected light (i.e., dark field detection mode). To obtain data indicative of the acquired image of the pattern in the illuminated region, sufficiently high resolution should be provided. To his end, the light collecting optics utilizes a high numerical aperture objective lens.

Analysis of the generated data consists of the so-called "modeling" of the pattern structure, and obtaining a discrete two-dimensional (or three-dimensional) array indicative of the scattering pattern. This data is used to simulate the dark-field scattering pattern within the collection angular field. The simulation results enable to determine the "background" intensity rising from the periodic pattern as the intensity lobe in the simulation/imaging plot, and collect light components propagating with the solid angle segment (s) of the collection angular field other than that of the "background" light components. This is implemented by locating an appropriate mask (filter) in an appropriate position within the optical path of the entire collected light (the so-called Fourier filtering).

It should be understood that each specific pattern structure is characterized by the solid angle segment of propagation of the "background" light components scattered from the periodic pattern. Hence, a library (database) can be previously designed containing a plurality of data records, each being indicative of the solid angle segments of the propagation of light scattered from a specific periodic pattern, with respect to a plurality of different pattern structures. These different pattern structures may be those produced at different manufacturing steps of a specific article (e.g., wafer), or may be associated with a plurality of different article types. This library actually presents reference data to be used for collecting the light components scattered from the illuminated region with said at least one predetermined solid angle segment of the certain collection angular field.

Thus, according to another aspect of the present invention, there is provided a method for inspecting a patterned structure with a certain maximum solid angle of collection of light scattered from the article to be inspected, said certain maximum solid angle of collection lying outside a solid angle of propagation of light specularly reflected from said patterned structure, the method comprising the steps of:

providing a database containing data representative of a plurality of solid angle segments of light propagation within said certain maximum solid angle of collection, said plurality of solid angle segments corresponding to a plurality of patterned structures including said patterned structure to be inspected, each of said solid angle segments corresponding to a direction of propagation of light components scattered from the corresponding patterned structure where the contribution of light scattered from the pattern is substantially minimal as compared to other solid angle segments of the solid angle of collection;

selecting from said database the data representative of said patterned structure to be inspected, which data is to be used for filtering from the entire light collected with said certain maximum collection angle the light components propagating with the corresponding solid angle segment, and allowing the detection of said light components.

The provision of the database utilizes detection of light scattered from each patterned structure in the plurality of structures (by bright-filed or high resolution dark-field detection mode), and analyzing data indicative thereof. The analysis procedure includes the steps of: modeling an image of the pattern in the form of a two- or three-dimensional array of discrete scatterers, determining the intensity distribution of light scattered from this modeled pattern within the maximum solid angle of collection.

According to yet another aspect of the present invention, there is provided an optical inspection apparatus for inspecting a patterned article, the apparatus comprising:

an illumination system for illuminating a region on the article;

a light collection system collecting light components scattered from the illuminated region at a certain collection angular field located outside a solid angle of propagation of specularly reflected light components, a filter operable in the optical path of the collected, scattered light components such as to separate therefrom light components propagating with a predetermined solid angle segment of said certain collection angular field;

a detection system comprising a detection unit for receiving a filtered part of the collected, scattered light and generating data representative thereof; and a control unit operating the filter in the optical path of the collected scattered light in accordance with predetermined data indicative of at least one solid angle segment of propagation of light scattered from the pattern in the illuminated region.

The predetermined data can be previously obtained either by the same optical inspection apparatus or by another inspection apparatus utilizing the bright field or high resolution dark field detection mode.

Preferably, the filter is in the form of a mask assembly including a plurality of different masks, each for filtering light components propagating with at least one specific solid angle segment of the maximum collection angular field, or corresponding to a specific pattern structure. Such a mask assembly can be selectively operated to locate the selective one of the masks in the optical path of the collected light. A mask can be of an LCD, mechanical, etc. type. The filter is preferably placed in the Fourier plane (conjugate plane) of the article plane.

The invention also provides, according to yet another its aspect, an optical inspection apparatus for inspecting a patterned article, the apparatus comprising:

(a) an illumination system for illuminating a region on the article;

(b) a light collection system comprising a first light collection arrangement collecting light components returned from the illuminated region, and a second light collecting arrangement collecting light components scattered from the illuminated region at a certain collection angular field located outside a solid angle of propagation of specularly reflected light components, (c) a filter selectively operable in the optical path of the collected, scattered light components for separating therefrom light components propagating with a predetermined solid angle segment of said certain collection angular field;

(d) a detection system comprising a fist detection unit that detects the light components collected by the first light collection arrangement and generates data representative thereof, and a second detection unit that detects a filtered part of the collected, scattered light and generates data representative thereof; and (e) a control unit, which is responsive to the data generated by the first detection unit for analyzing said data and operating the filter accordingly.

According to yet another aspect of the present invention, there is provided a control unit to be used in a system for optical inspection of a patterned structure with a certain maximum solid angle of collection of light scattered from the structure to be inspected, said certain maximum solid angle of collection lying outside a solid angle of propagation of light specularly reflected from the structure, the control unit comprising a memory that stores a database containing a plurality of data records corresponding to a plurality of patterned structures including said patterned structure to be inspected, wherein each data record contains data indicative of at least one solid angle segment of said certain maximum solid angle of collection corresponding to a direction of propagation of light components scattered from the corresponding patterned structure where the contribution of light scattered from the pattern is substantially minimal, as compared to other solid angle segments of the maximum solid angle of collection.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

More specifically, the present invention is used for inspecting semiconductor wafers (constituting a patterned article, or a pattern structure considering the structure produced by one of the manufacturing steps applied to the same article), and is therefore described below with respect to this application.

Figure 1:
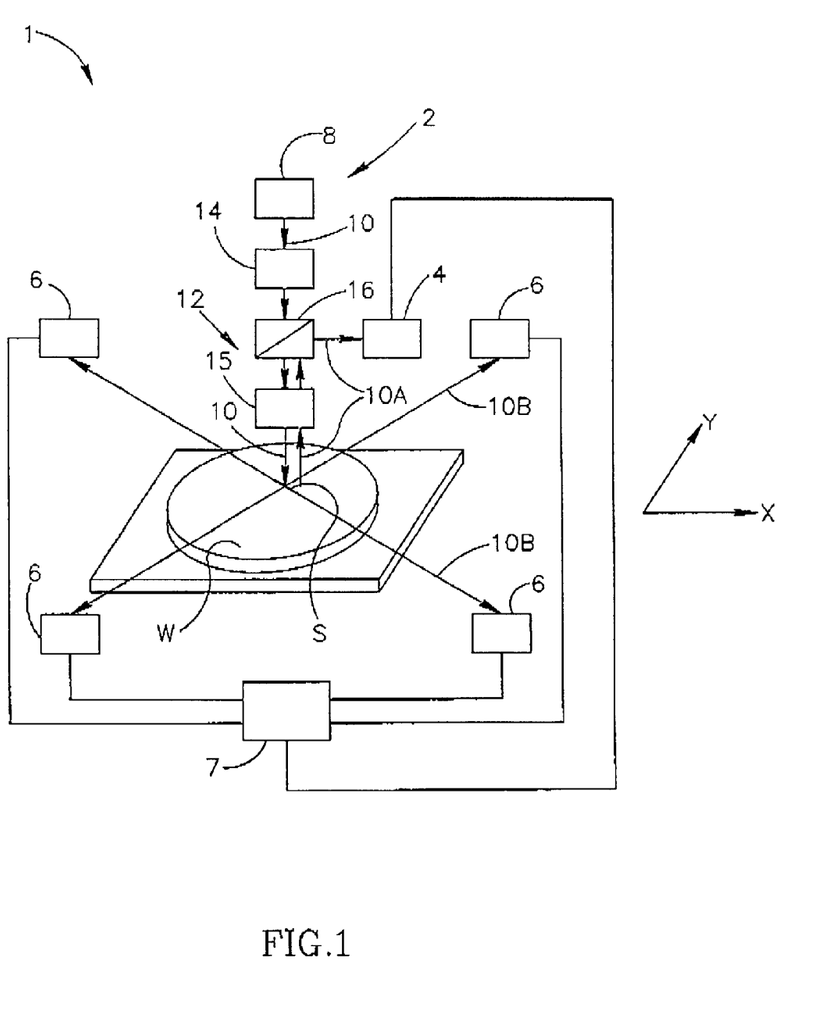
FIG. 1 schematically illustrates the main components of an optical inspection apparatus according to one embodiment of the invention.

Referring to FIG. 1, there is illustrated one possible example of an optical inspection apparatus 1 according to the invention associated with a wafer W to be inspected. The apparatus 1 comprises an illumination system 2, and a light collection/detection system. The latter is composed of a first light collecting optics associated with a detection unit 4 operating in a bright field imaging mode, and a second light collecting optics (not shown here) associated with detection units 6 each operating in a dark field imaging mode. In the present example, four such detection units 6 are provided, each associated with its corresponding light collecting optics. Output circuits (not shown) of the detection units 4 and 6 are coupled to a control unit 7. The control unit 7 is typically a computer system, appropriately equipped with hardware and operated by suitable software, so as to successfully analyze data coming from the detection units, as will be described more specifically fiber below.

The illumination system 2 comprises a light source 8, for example a laser, emitting a beam of light, generally at 10, and light directing optics 12. If a laser is used as a light source, the optics 12 has a suitable scanning means 14 (for example an acousto-optic element) mounted in the optical path of the beam 10, and a focusing optics 15 (i.e., objective lens). When operating with the laser illumination, a high numerical aperture objective lens is used to provide high resolution of acquired images. The scanning means 14 causes the beam 10 to move in a scanning direction (i.e. along the X-axis), while the wafer W is supported on a translational stage for movement along the Y-axis. The scanning means 14 and focusing optics 15 operate together to focus the beam 10 onto a scan line S (constituting an illuminated region) on the wafer's surface. Obviously, any other suitable scanning means could be used, such as a rotating mirror. The provision of any scanning means is optional, and a "non-scanning" beam could be used for the same purpose, i.e., for illuminating the line on the wafer's surface. The propagation of light is shown here schematically, solely in order to facilitate the illustration of the main components of the apparatus 1.

In the present example of FIG. 1, the illumination system 2 provides normal incidence of the beam 10 onto the wafer W. Consequently, the light directing optics 12 comprises a beam splitter 16 for separating the incident and reflected light components. It should, however, be noted that the incident beam can be directed onto the wafer's surface at a certain angle of incidence. It should also be noted that, in general, the bright-field based system could utilize either the same illumination path as that used for the dark field imaging, or its own illumination path.

As indicated above, in the present example the detection unit 4 operates in the bright field imaging mode, namely, collects light components 10a specularly reflected from the scan line S, wherein the specular reflected light propagates within a certain solid angle. The detection unit 4 comprises a suitable detector, e.g., PMT, CCD or pin-diode, capable of receiving the collected specularly reflected light and generating data indicative of an image of the scan line S.

Each of the detection units 6 operates in the dark field imaging mode, namely, collects light components 10b scattered from the wafer's surface at the azimuth and elevation different from those where the most specular reflection occurs.

Generally speaking, the light collecting optics of the detection unit 6 collects light with a certain maximum solid angle of collection (constituting a collection angular field), as will be described further below. The detection unit 4 is used for acquiring an image of the pattern structure, enabling the analysis of this image and the determination of at least one solid angle segment of the collection angular field to be used for detecting light with the detection unit 6. This at least one solid angle segment is that where the contribution of light returned from the pattern is minimal as compared to that of the other solid angle segments of the collection angular field.

Thus, although in the example of FIG. 1 the detection unit 4 operates with the bright filed detection mode, to enable the above image acquisition and analysis, high-resolution dark field detection can be used as well. A high-resolution dark field detector can be used for both the imaging and inspection purposes.

Figure 2:
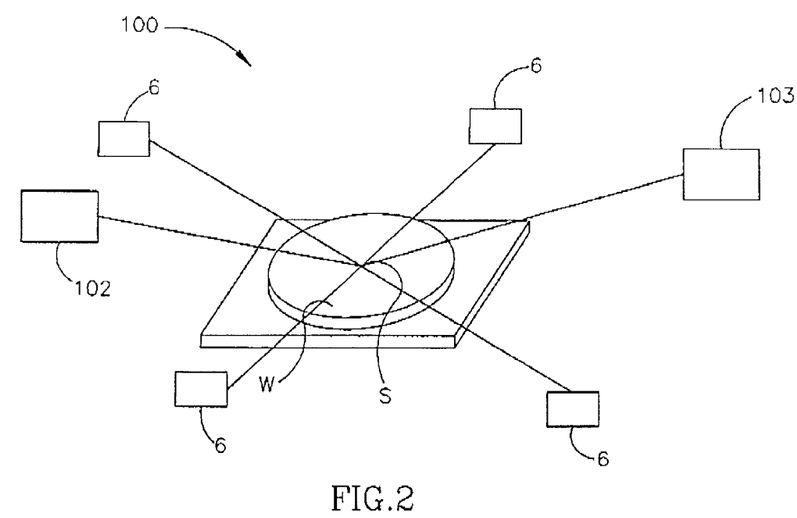
FIG. 2 illustrates an optical inspection apparatus according to another embodiment of the invention.

The invention may utilize a detector of an auto-focusing system typically installed in an optical inspection apparatus as the bright-field detector for imaging the pattern. This is illustrated in FIG. 2 showing an optical inspection apparatus, generally designated 100, that comprises an illumination system 102, an auto-focusing system 103 operating with a bright-field detection mode and four dark-filed based detection units 6. The detectors 6 and that (not shown) of the auto-focusing system 103 are connected to the control unit 7. The detector of the system enables imaging of the illuminated region on the article, which image is analyzed by the control unit to determine a collection angle of the maximum collection angular field which is to be used for detecting light with the detection unit 6.

Figure 3:
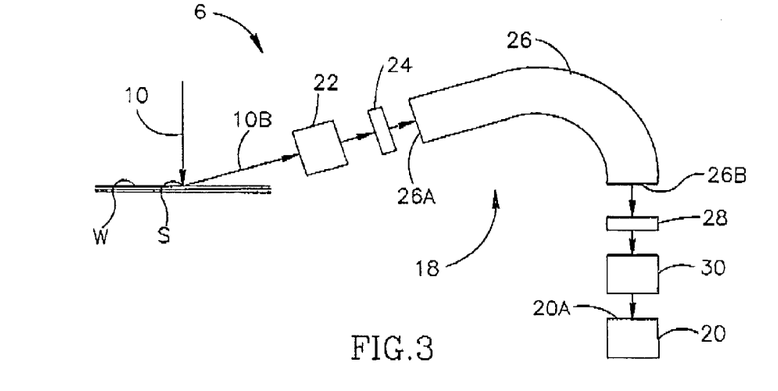
FIG. 3 schematically illustrates the main components of a detection unit of the apparatus of FIG. 1.

In both examples of FIGS. 1 and 2, the four detection units 6 have similar constructions, and therefore the main components of only one will now be described with reference to FIG. 3. The detection unit 6 comprises a light collection system 18 and a detector 20, which may be of any suitable kind, e.g., PMT, whose construction and operation are known per se.

In the exemplified preferred embodiment, the light collection system 18 includes collecting optics 22 (constituting a second light collecting optics), a coherent (imaging) fiber bundle 26 (constituting image transmission means) and a mask assembly 28 (constituting a filter) which is followed by an optical system 30. While not a necessary element, the preferred embodiment includes a polarizer 24 inserted in the light path of the optics 22. The principles of operation of the coherent fiber are known per se, and therefore need not be specifically described, except to note the following. A coherent fiber bundle is used for transmission of images. The relative positions of individual fibers in the coherent fiber bundle is maintained, and, due to this fact, the fiber bundle provides the desired linear correlation between input and output signals.

Thus, the incident light 10 impinges onto the scan line S. As shown in FIG. 1, the specularly reflected light components 10a are collected by the optics 3a to be received by the detection unit 4. Turning to FIG. 3, the light components 10b, scattered from the pattern and anomalies that may occasionally occur on the wafer's surface within the scan line S, propagate towards the optics 22. The light components 10b that are scattered from the scan line S and propagate with a certain maximum solid angle (collection angular field) are collected by the optics 22 and directed into the polarizer 24. The polarizer 24 is operated by a suitable driver (not shown) for movement in a manner to be positioned either in or out of the optical path of the light ensuing from the collecting optics 22, Additionally, the polarizer 24, when being installed in the optical path, is rotatable in a manner to change the orientation of the plane of its preferred transmission (preferred polarization). The displacement of the polarizer 24 affects light passing therethrough. Since the pattern may have a high polarization degree representing a so-called "polarized noise", the displacement of the polarizer affects the signal-to-noise ratio in the light component propagating towards the detector. Additionally, a leaning mode may be applied to the specific kind of article prior to its inspection. This enables a certain polarization signature in the light component returned from the pattern to be expected and, therefore, by changing the orientation of the polarizer 24, to detect differences (defects), if any.

Figure 4:
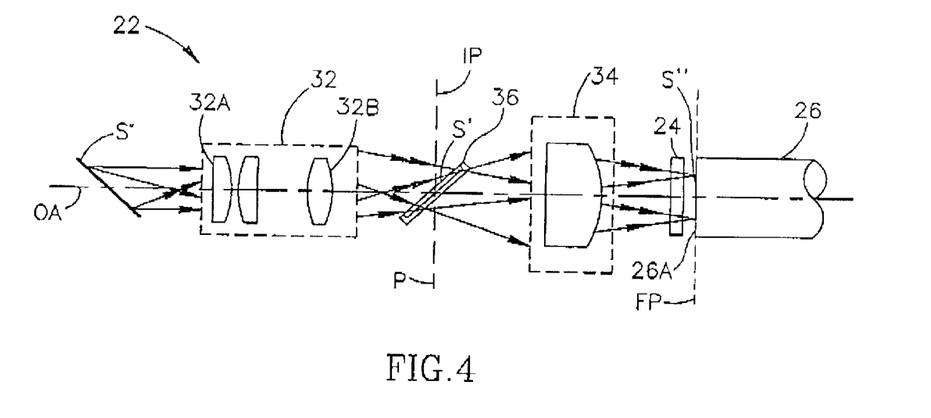
FIG. 4 schematically illustrates the construction of light collecting optics of the detection unit of FIG. 2.

The light collecting optics 22 is designed so as to form an angular image of the scan line S which is then transmitted towards the detector 20 through the fiber bundle 26. As shown in FIG. 4, the light collecting optics 22 comprises first and second lens assemblies 32 and 34, and a slit 36 located in a front focal plane P of the lens assembly 34. The light propagation through the lens assemblies 32 and 34 defines an optical axis OA. The lens assembly 32 is positioned to collect light components scattered from the scan line S and propagating with a certain solid angle. The dimensions of a first glass surface 32a of the lens assembly 32 defines the value of the solid angle of collection of the optics 22, which is the maximum collection angle (the so-called "collection angular field") of the entire detection unit 6. The lens assembly 32 is designed to form a real image S' of the scan line S in an image plane IP. The image plane IP substantially coincides with the front focal plane P of the lens arrangement 34. The slit 36 is shaped and dimensioned similar to that of the real image S', and is installed at the location of the expected image. As for the lens assembly 34, it forms from the real image S' of the scan line S an angular image S" thereof Each point of the angular image S" is formed by a light component coming from any point of the scan line S and propagating with a segment of the maximum collection angle. Each such segment of the maximum collection angle is projected onto a corresponding point (fiber) on the input surface 26a of the fiber bundle 26, and is transmitted by the fiber bundle into the same angle ensuing from the corresponding point On an output surface of the fiber bundle.

The provision of the slit 36 is based on the following. The illumination unit, due to reflection occurring therein, produces an additional undesirable image of the scan line (a so-called "ghost") on the surface of the wafer. This undesirable image will also generate returned light propagating towards the light collecting optics. The slit 36 so designed and positioned, allows the passage of the collected light representative of the real image S' of the scan line S to the lens assembly 34, and blocks the passage of any light other than that associated with the image S'.

A surface 26a defined by the front end (with respect to light propagation) of the fiber bundle 26, is located in a focal plane FP of the entire collecting optics 22, defining thereby the most desirable location for the system's entrance pupil. Such a design of the collecting optics 22 and its position relative to the fiber bundle 26 enables the resolution of the light collection system 18 to be significantly increased, and allows for optimizing the fiber bundle operation. The diameter of the fiber bundle 26 should preferably slightly exceed that defined by the cone of the maximum collection angle, so as to allow all the collected light beams (i.e. all the solid angle segments of the maximum collection angle) to enter the fiber bundle 26.

Thus, the light collecting optics 22 forms the angular image S" of the scan line S, and directs the collected light representative of this image into the fiber bundle 26. Each point of the image S" is representative of a certain angle of propagation of the collected light component (within the collection angular field) scattered from any point on the scan line S. Each angular light component is projected onto a corresponding point (fiber) on the input surface 26a of the fiber bundle 26, and is transmitted by the fiber bundle into the same angle ensuing from the corresponding point on an output surface of the fiber bundle. This technique ensures the same angular field of view of all points along the scan line S, and of all the detection units 6, thereby increasing the signal-to-noise ratio in difference-indicative signals that can be detected when comparing data generated by all the detection units 6.

Figure 5A:
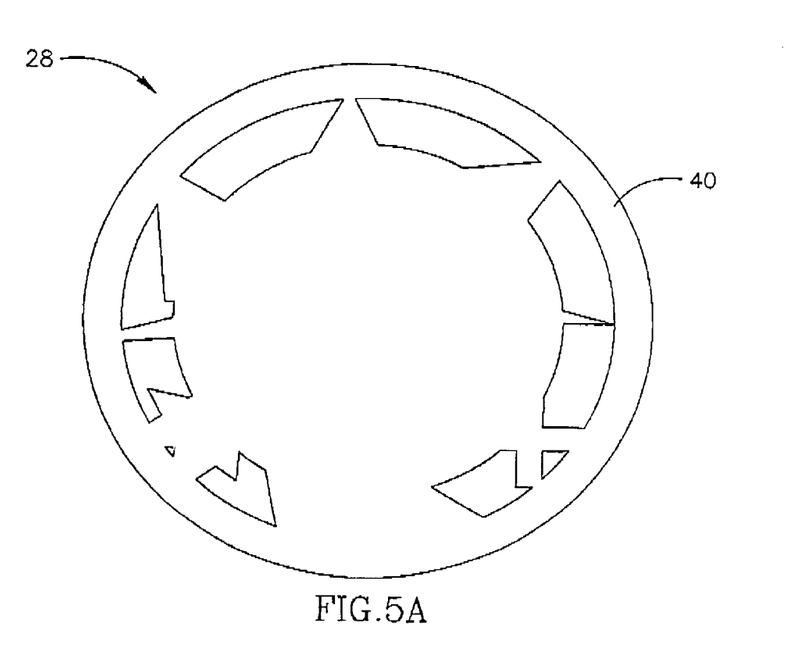
FIG. 5 schematically illustrates an example of a mask assembly suitable to be used as a filter in the apparatus of FIG. 1.

Turning now to FIG. 5a, the mask assembly 28 is composed of a plurality of differently designed masks formed in a common disc-like opaque plate 40. This may be, for example, a metal disk with holes or a glass-with-chrome mask. The disc 40 is operated by its motor, which is not specifically shown here, for rotation in a plane perpendicular to the long axis of the fiber bundle so as to selectively locate one desired mask in the optical path of the propagating light.

In the present example of FIG. 5a, the plurality of different masks is arranged like a continuous pattern formed by transparent and opaque regions, and extending along the circumferential region of the disc 40. Each portion of the pattern is formed by a different combination of locally adjacent transmitting and opaque regions, and represents one mask from the plurality of different masks formed by different portions of the pattern. One transmitting/opaque region, whilst being combined with its left-side neighboring region and whilst being combined with its right-side neighboring region, may form two different portions of the pattern, respectively. By rotating the disk about its axis, a different portion of the pattern (mask) is located in the optical path of the collected light impinging on the disk.

Figure 5B:
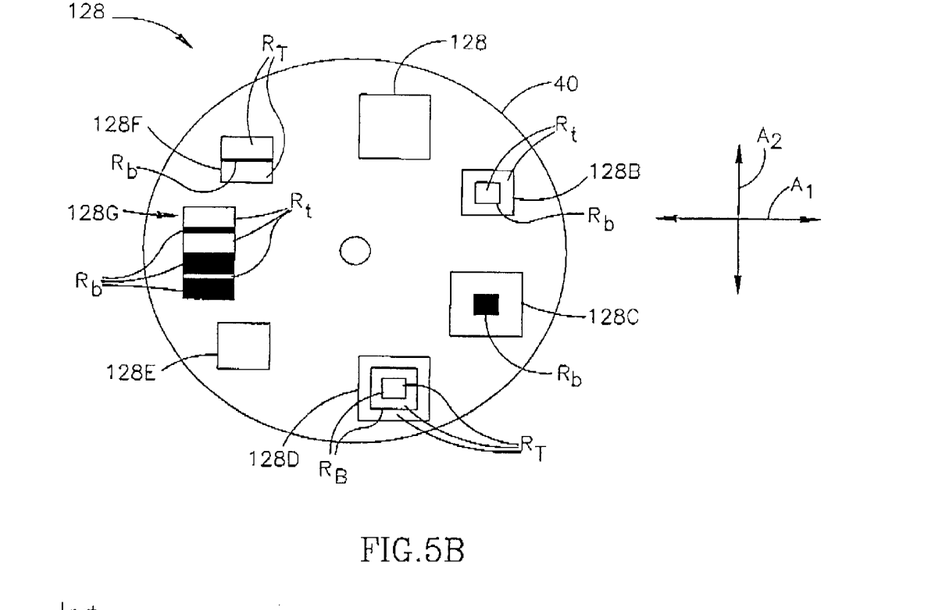

FIG. 5b illustrates a mask assembly 128 having a somewhat different design as compared to the mask assembly 28 in FIG. 5a. Here, the mask assembly is composed of several differently designed masks, seven in the present example, designated respectively 128a–128g, which are formed in the common disc-like opaque plate 40. In the operational position of the mask assembly 128, one of the masks 128a–128g is installed in the optical path of the light ensuing from the fiber bundle 26. Each of the masks 128a and 128e represents an aperture that defines a certain solid angle of collection smaller than the maximum collection angle defined by the first glass surface 32a of the lens arrangement 32. By placing one of the masks 128a and 128e in the optical path of the light ensuing from the fiber bundle 26, one certain solid angle segment of the maximum collection angle may be picked out. The masks 128b, 128c, 128d, 128f and 128g have different patterns, each formed of regions $R_t$ and $R_b$ which respectively, transmit and block the light impinging on the mask. Each of these masks, when in its operative position (i.e. located in the optical path of the light ensuing from the fiber bundle), is capable of cutting off and picking out one or more solid angle segments.

Generally speaking, each of the masks defines at least one transmitting region with respect to the collected light corresponding to at least one solid angle segment of the maximum collection angle (collection angular field). In the operational position of the mask assembly 28 (or 128), one of the masks is installed in the optical path of the light ensuing from the fiber bundle 26, namely in the conjugate plane (or Fourier plane) of the wafer plane, and allows the propagation of light components at the corresponding solid angle segment(s) towards the detector 20.

The provision of the mask assembly comprising the plurality of different masks allows for selectively varying the collection angle of the entire detection unit 6, thereby enabling the customized light collection to be provided. It is important to note that such a mask assembly provides for solid angle variations simultaneously along two mutually perpendicular axes, shown as $A_1$ and $A_2$, resembling elevation and azimuth scattering angles.

For the purposes of the present invention, the light components scattered from the pattern present "noise" to be filtered out of the detected signals, while the light components scattered from the anomalies present "defects" to be detected. To determine which solid angle segment should be filtered out of the light propagating towards the detector 20, or which solid angle segment should be chosen as the customized light collection, the knowledge of the wafer's pattern is needed. This pattern can be seen in the bright field image of the scan line obtained with the detection unit 4 (FIG. 1), with that of the auto-focusing system 103 (FIG. 2), or with a high-resolution dark field detector.

Figure 6A:
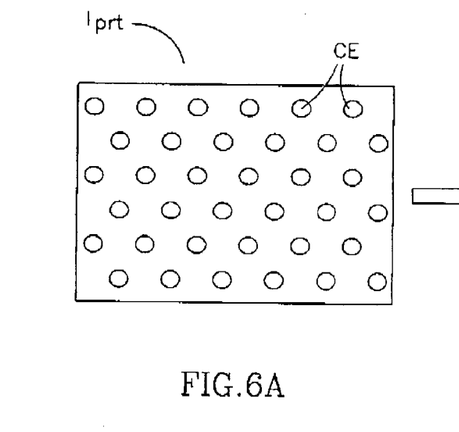
FIGS. 6a and 6b illustrate the real bright field image of an illuminated region, and an "idealized", simulated image thereof, respectively.
Figure 6B:
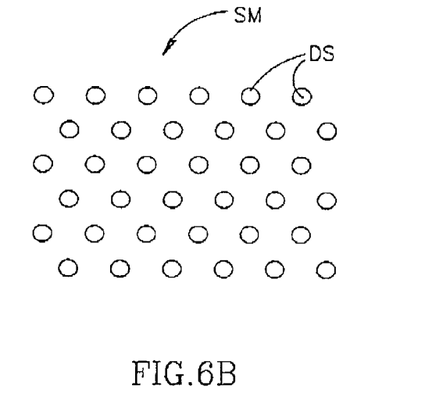
Figure 7A:
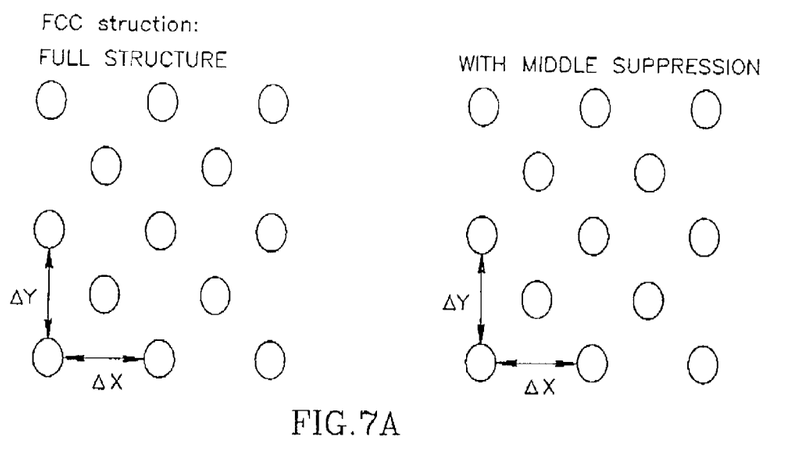
FIGS. 7a to 7e illustrate simulated images of five different pattern structures, respectively.
Figure 7B:
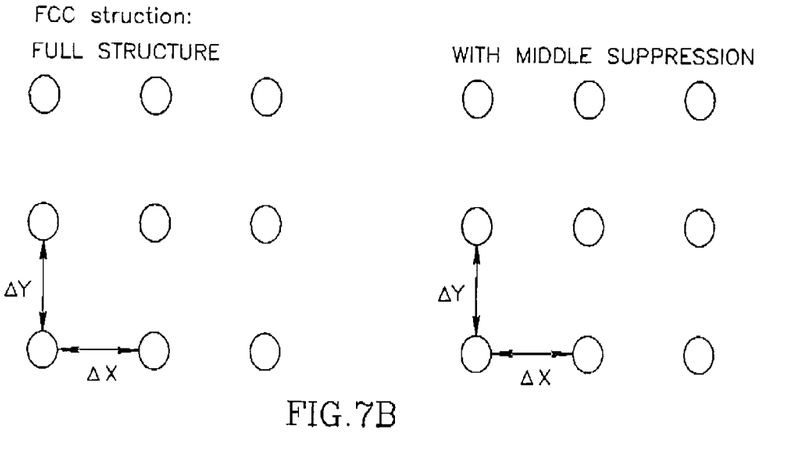
Figure 7C:
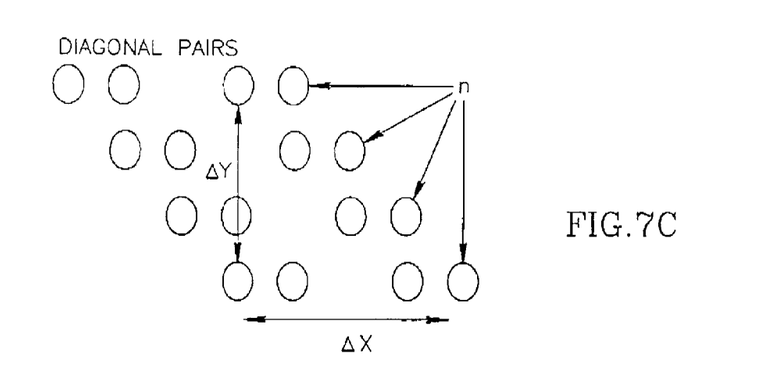
Figure 7D:
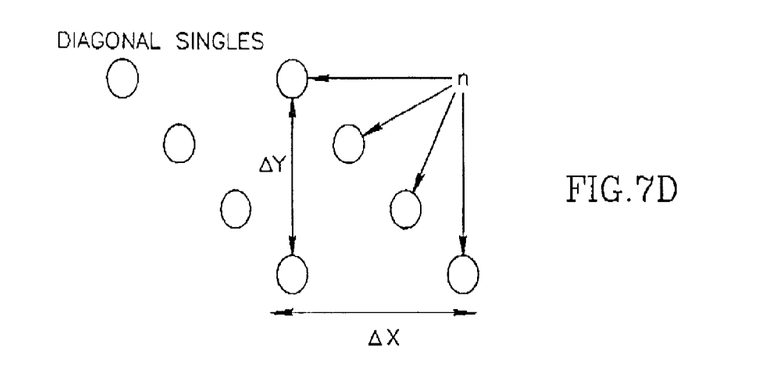
Figure 7E:
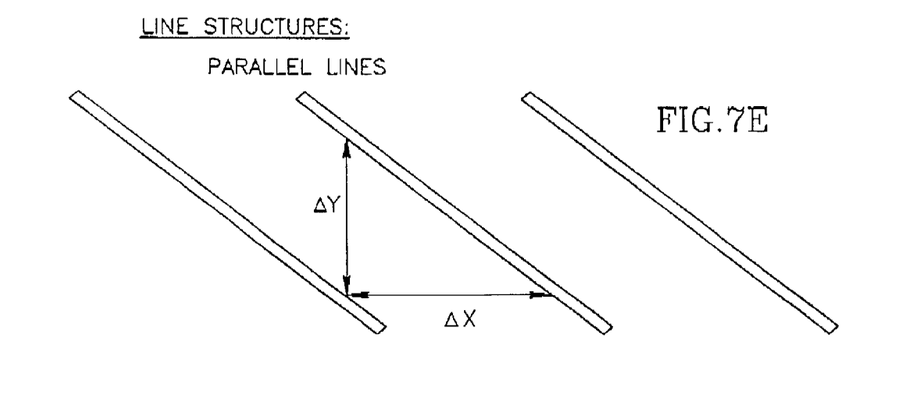

Thus, the data indicative of this image is appropriately generated and transmitted to the control unit 7, where this data is analyzed, and a "modeled", simulated image of the pattern is constructed. This is illustrated in FIGS. 6a and 6b. FIG. 6a shows the real image $I_{pat}$ of the illuminated region in the form of almost perfectly periodical two-dimensional pattern of a basic cell element CE. The modeling of the pattern structure involves replacing every element CE in the repeated cell by a point-scattering object. FIG. 6b shows a model SM of the structure $I_{pat}$ formed of discrete (point) scatters DS.

The step of image modeling includes the following stages:

(1) Basic cell dimensions recognition, consisting of correlating the matrix of the image $I_{pat}$ with itself, and determining the first maximum with respect to the correlation shift in both lateral dimensions, which does not represent the zero shift, this first maximum corresponding to the cell's basic dimensions.

(2) Cell structure recognition, during which a basic cell structure may be chosen from a known list of cell structures such as FCC, BCC, etc.), the image is constructed using this structure and its dimensions determined in stage (1), and the outcome is correlated with the original image. The structure that gives the highest correlation value is the desired cell structure.

(3) Assuming the point scattering for each basic element CE.

The result of the image modeling step is the two-dimensional discrete scattering function $S_{ij}$, which represents the scattering pattern from the wafer's surface along with the proportional scattering intensities.

Data indicative of the distances between two repeated discrete scatters along the X- and Y-axes (so-called "pitch") in the known structure is previously entered and stored in the memory of the control unit. This is illustrated in FIGS. 7a–7e showing four examples of the known structures, namely, FCC, BCC, diagonal and line structures, respectively. Here, $\Delta x$ and $\Delta y$ are the structure pitches along the X-and Y-axes.

In order to consider a realistic scattering pattern, the actual shape and size of the illumination function should be projected on the scattering plane. In other words, the step of periodic scattering calculation is carried out. For this purpose, the illumination finction is set, and the discrete sum of the scattering from each element that encountered this function is performed.

(A) Setting the illumination function

The illumination function model is taken as the model of a diffraction limited spot incident on the wafer, thereby obtaining a two-dimensional discrete function, $I_{ij}$, which represents the incident intensity on each discrete site on the wafer's surface. The discrete illumination function usually consists of a truncated Gaussian beam holding various parameters such as spot size, incident angle, phase distortion along the spot size and position along the scan line. The spot impinging on the wafer is a Fourier transform of the truncated Gaussian characterized by the following parameters:

spot size at 1/e² for both major axes (scan and cross scan);

apodization width and its position with respect to the spot's maximum intensity;

spot telecentricity, simulated as linear phase difference along one or both of the spot major axes;

general phase distortion across the spot; and length of the scan line.

The outcome of the above step is a two-dimensional discrete function $I_{ij}$ which represents the incident intensity on each discrete site on the wafer's surface.

Figure 8:
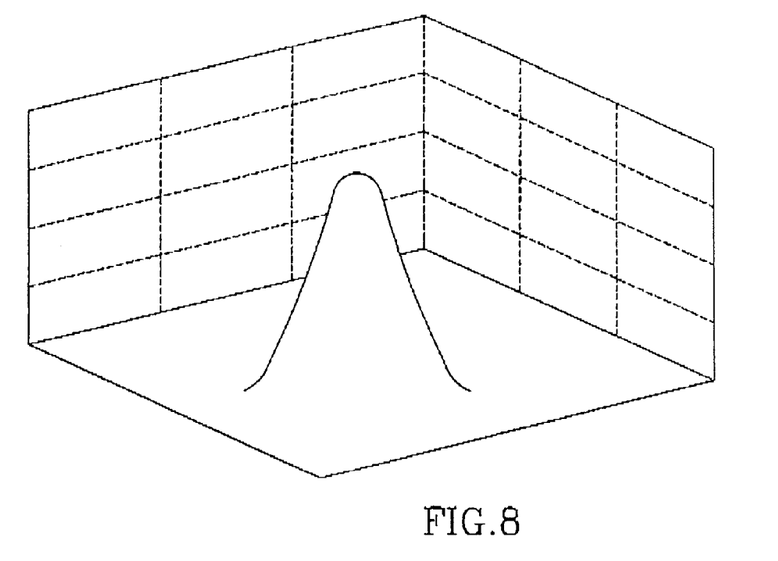
FIG. 8 schematically illustrates an illumination function projected on a scattering plane, used to simulate a Gaussian beam impending on the surface of an article.

FIG. 8 illustrates an example of a simple Gaussian spot. Here, the distribution RMS is 10 μm, thus modeling a spot size of 20 μm, the total intensity being normalized to 1.

The resulting scattering intensities of each point scattering object on the plane are then computed by point to point multiplication of the scattering structure $S_{ij}$ and illumination function $I_{ij}$, that is:

$$P_{ij} = S_{ij} I_{ij}$$

Figure 9:
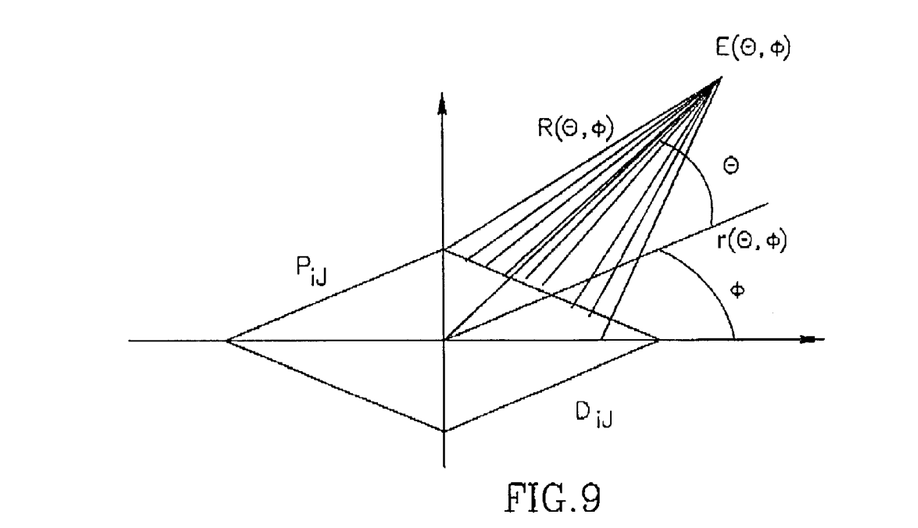
FIG. 9 schematically illustrates the geometry of the scattering problem used for simulation purposes.

(B) Summing up the scattering of Rayleigh point scatters distributed on the surface on to every angle in the collection angular field, utilizing the geometry of the scattering problem is illustrated in FIG. 9.

Using the vector wave formalism, the resulting far field distribution is computed by an amplitude and phase summation of the surface field contribution to every point in a large sphere surrounding the reflecting pattern. As known, the general vector form of the far field electric field due to a small dipole is given by:

$$E = k^2 (r \times p) \times r \frac{e^{ikr}}{r^3}$$

wherein r is the vector defining the detector's position; p is the vector defining the dipole's vibration orientation; and k is the wave number ($|k|=2\pi/\lambda$, where λ is the beam's wavelength). It should be noted that instead of point scattering object, the form factor can be considered, that is:

$$\int p(r) e^{ikr}$$

For a given incident wave polarization $p_0$, the assumption that no cross polarization pattern exists states that up to a scaling factor $p=p_0$.

The field summation is performed as follows:

$$E(\theta, \varphi) = \sum_{i,j} k^2 (r_{i,j} \times p) \times r_{i,j} \cdot P_{i,j} \frac{e^{-ikr_{i,j}(\theta,\varphi)}}{r_{i,j}}$$

wherein:

$$r_{ij}(\theta,\phi) = R(\theta,\phi) - D_{ij}$$

$$D_{ij} = (i,j,0)$$

$$R(\theta,\phi) = (R\sin(\theta)\cos(\phi), R\sin(\theta)\sin(\phi), R\cos(\theta))$$

is and R is the detector's distance.

The resulting intensity distribution in the detector's sphere is given by:

$$I(\theta,\phi) = |E(\theta,\phi)|^2$$

Figure 10A:
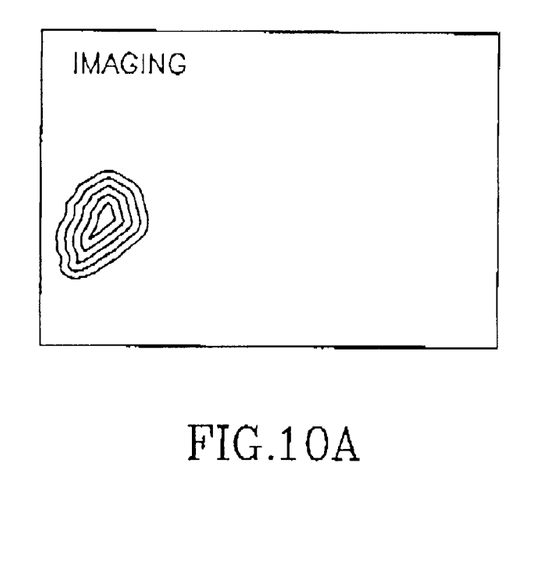
FIGS. 10a and 10b illustrate, respectively, the simulation scattering results and imaging of the intensity profile.
Figure 10B:
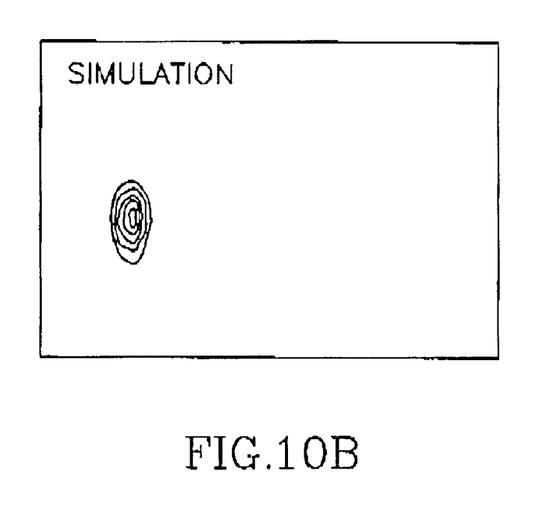

The resulting simulated dark field scattering pattern usually consists of several intense lobes located at specific angles. This simulation model pattern can be compared to an imaging of the actual scattering intensities along the collection angular field. FIGS. 10a and 10b illustrate, respectively, the actual pattern seen using the imaging fiber, and that obtained by the simulation of scattering from the wafer structure. It is thus evident that by blocking the "Background" intensity rising from the periodic pattern seen as the intense lobe in the simulation imaging plot, the signal-to-noise ratio in the detected signal can be significantly increased.

Turning back to FIGS. 5a and 5b, an effective dark field mask can be found based on the optimization algorithm that minimizes the structure scattering intensity, while maximizing the angular vacancy of the collection angular field. This effective mask is used while scanning the wafer.

It is important to note that most of patterned articles are manufactured in series. Therefore, each article type, or a structure obtained with one of the manufacturing steps applied to the same article, can be previously imaged to determine solid angle segments corresponding to the propagation of light scattered from the pattern within the maximum collection angle of the given optics. Based on these data, a library can be prepared and stored in the memory of the control unit. In this case, there is actually no need for applying a specific detection mode (bright field or dark field detection) for acquiring and analyzing an image of the structure to be inspected, but to rather utilize the reference data from the library to operate the mask assembly (filter) accordingly. Articles of different types are different patterned structures, e.g., the same wafer, but after different manufacturing steps, namely, with differently patterned uppermost layers.

It should be noted, although not specifically shown, that the mask assembly 28 (or 128) could be accommodated in the optical path of the collected light upstream of the fiber 26. In this case, the mask assembly should be located in the focal plane FP of the light collecting optics 22, and the fiber bundle 26 may and may not be an imaging fiber.

It should also be noted that such a mechanical filter may be replaced by a micro electromechanical structure (MEMS) or a programmable liquid crystal display (LCD) whose construction and operation are known per se. The LCD segments are light valves which, when in the open mode, transmit or reflect light (depending on the kind of a liquid crystal material used therein), and, when in the closed mode, block light. A spatial filter in the form of a transmitting LCD is disclosed for example in U.S. Pat. No. 5,276,498.

It should be understood that, if a reflective LCD or EMS is used as the mask assembly, the fiber bundle is positioned so as to receive collected light reflected from the filter (selected mask). The fiber bundle is not necessarily of the imaging type.

Referring back to FIG. 3, the optical system 30 is designed so as to project the light collected by the mask assembly 28 (or 128) onto the entire sensing surface of the detector 20. For example, the system 30 may be a telecentric imaging system, wherein the sensing surface of the detector 20 is positioned at the location of the system's entrance pupil. The principles of telecentric imaging optics are known per se and therefore need not be more specifically described, except to note that such optics avoid distance-introduced magnification changes and maintain the same magnification of the image over a wide range of distances along the optical axis of the system. The provision of the optics 30 that projects the light collected by the mask assembly onto the entire sensing surface is associated with the following. The sensing surface of any detector typically has non-uniform sensitivity distribution. If the spatially separated light cones (by the mask) were projected onto correspondingly separated regions on the sensing surface, detected differences in the output signals produced by the detector might have been associated with the sensitivity differences of these regions and not with the differences in the scattered light. To avoid such an undesirable dependence between the output signal and the selected collection angle, optics 30 provides the illumination of the entire sensing surface by each one of the collected light components (selected angles).

Those skilled in the art will readily appreciate that various modifications and changes can be applied to the preferred embodiment of the invention as hereinbefore exemplified without departing from its scope defined in and by the appended claims. For example, the collection/detection assembly aimed at imaging purposes may operate with high-resolution bright or dark field detection mode. The fiber bundle may be replaced by any other suitable image transmission means, e.g., a relay optics which is typically a multilens system serving for maintaining a certain numerical aperture of the light propagation. The mask assembly may contain several spatially separated masks made in a common disk, rather than being in the form of the continuous pattern of transmitting and opaque regions, and may be installed either in front of or after the image transmission means.

What is claimed is:

1. A method for optical inspection of a patterned article, the method comprising the steps of:
   (i) illuminating a region on the article with incident light to produce light returned from the illuminated region;
   (ii) acquiring an image of the illuminating region, and generating data representative thereof,
   (iii) analyzing the generated data and determining intensity distribution of light components scattered from the pattern of the illuminated region within a certain collection angular field outside a solid angle of propagation of specularly reflected light;
   (iv) based on the determined distribution, filtering light collected with said certain collection angular field, so as to collect light components scattered from the illuminated region and propagating with at least one predetermined solid angle segment of said certain collection angular field, and to direct the collected light components to a detection unit.

2. The method according to claim 1, wherein the step of analyzing the generated data comprises the step of:
   constructing a model of the pattern structure of the illuminated region, such as to obtain a discrete array indicative of the scattering pattern;
   simulating a dark-field scattering pattern within said certain collection angular field;
   based on the simulation results, determining background intensity rising from the periodic pattern, so as to determined said at least one solid angle segment of collection as that where said background intensity is minimal as compared to other segments of said certain solid angle.

3. The method according to claim 2, wherein the construction of the model comprises the steps of:
   determining basic cell dimensions, wherein said basic cell is an element of the pattern repeated numerous times in both lateral dimensions;
   determining a cell structure in the pattern; and
   assuming point scattering for each basic cell.

4. The method according to claim 1, wherein the acquired image is obtained with a bright field detection mode.

5. The method according to claim 1, wherein the acquired image is obtained with a dark field detection mode.

6. The method according to claim 1, wherein said pattern article progresses on a production line is a stream of similar patterned articles, steps (ii) and (iii) being performed only with respect to the first patterned article in the stream.

7. A method for inspecting a patterned structure with a certain maximum solid angle of collection of light scattered from the article to be inspected, said certain maximum solid angle of collection lying outside a solid angle of propagation of light specularly reflected from said patterned structure, the method comprising the steps of:
   providing a database containing data representative of a plurality of solid angle segments of light propagation within said certain maximum solid angle of collection, said plurality of solid angle segments corresponding to a plurality of patterned structures including said patterned structure to be inspected, each of said solid angle segments corresponding to a direction of propagation of light components scattered from the corresponding patterned structure where the contribution of light scattered from the pattern is substantially minimal as compared to other solid angle segments of the solid angle of collection;
   selecting from said database the data representative of said patterned structure to be inspected, which data is to be used for filtering from the entire light collected with said certain maximum collection angle the light components propagating with the corresponding solid angle segment, and allowing the detection of said light components.

8. An optical inspection apparatus for inspecting a patterned article, the apparatus comprising:
   an illumination system for illuminating a region on the article;
   a light collection system collecting light components scattered from the illuminated region at a certain collection angular field located outside a solid angle of propagation of specularly reflected light components,
   a filter operable in the optical path of the collected, scattered light components such as to separate therefrom light components propagating with a predetermined solid angle segment of said certain collection angular field;
   a detection system comprising a detection unit for receiving a filtered part of the collected, scattered light and generating data representative thereof; and
   a control unit operating the filter in the optical path of the collected scattered light in accordance with predetermined data indicative of at least one solid angle segment of propagation of light scattered from the pattern in the illuminated region.

9. The apparatus according to claim 8, and also comprising a light collection/detection system for acquiring an image of the illuminated region and generating data representative thereof to be analyzed by the control unit for determining said predetermined data.

10. The apparatus according to claim 9, wherein the acquired image is obtained with a bright field detection mode.

11. The apparatus according to claim 9, wherein the acquired image is obtained with a dark field detection mode.

12. The apparatus according to claim 9, wherein the collection and detection of said light returned from the illuminated region utilizes a dark field detection mode.

13. An optical inspection apparatus for inspecting a patterned article, the apparatus comprising:

(a) an illumination system for illuminating a region on the article;
(b) a light collection system comprising a first light collection arrangement collecting light components returned from the illuminated region, and a second light collecting arrangement collecting light components scattered from the illuminated region at a certain collection angular field located outside a solid angle of propagation of specularly reflected light components,
(c) a filter selectively operable in the optical path of the collected, scattered light components for separating therefrom light components propagating with a predetermined solid angle segment of said certain collection angular field;
(d) a detection system comprising a first detection unit that detects the light components collected by the first light collection arrangement and generates data representative thereof, and a second detection unit that detects a filtered part of the collected, scattered light and generates data representative thereof; and
(e) a control unit, which is responsive to the data generated by the first detection unit for analyzing said data and operating the filter accordingly.

14. The apparatus according to claim 13, wherein said filter comprises a plurality of different masks, each for filtering at least one solid angle segment of the said collection angular field and allowing its propagation towards the second detection unit, while blocking other solid angle segments of the collection angular field.

15. The apparatus according to claim 14, wherein said plurality of different masks present a continuous pattern formed by transparent and opaque regions and extending along a circumferential region of a disc-like plate.

16. The apparatus according to claim 14, wherein the different masks are arranged in a spaced-apart relationship along a circumferential region of a disc-like plate.

17. The apparatus according to claim 13, wherein the analyzes of said data generated by the first detection unit consists of determining background intensity rising from the periodic pattern, so as to determine said at least one solid angle segment of collection as that where said background intensity is minimal as compared to other segments of said certain collection angular field, said filter being operated to filter from the entire collected scattered light those light components which propagate with said at least one solid angle segment.

18. The apparatus according to claim 17, wherein the control unit comprises a processing utility that receives the data generated by the first detection unit and indicative of an image of the pattern in the illuminated region, constructs a model of the pattern structure of the illuminated region in the form of a discrete array indicative of the scattering pattern, and simulates a dark-field scattering pattern within said certain collection angular field.

19. The apparatus according to claim 13, and also comprising at least one additional detection unit for detecting light scattered from the illuminated region, the at least two detection unit detecting light parts collected at different azimuth angles.

20. The apparatus according to claim 13, wherein the collection and detection of said light returned from the illuminated region utilizes a bright field detection mode.

21. A control unit to be used in a system for optical inspection of a patterned structure with a certain maximum solid angle of collection of light scattered from the structure to be inspected, said certain maximum solid angle of collection lying outside a solid angle of propagation of light specularly reflected from the structure, the control unit comprising a memory that stores a database containing a plurality of data records corresponding to a plurality of patterned structures including said patterned structure to be inspected, wherein each data record contains data indicative of at least one solid angle segment of said certain maximum solid angle of collection corresponding to a direction of propagation of light components scattered from the corresponding patterned structure where the contribution of light scattered from the pattern is substantially minimal, as compared to other solid angle segments of the maximum solid angle of collection.

* * * * *